United States Patent
Chin et al.

(10) Patent No.: US 10,561,146 B2
(45) Date of Patent: Feb. 18, 2020

(54) STAR POLYMERS WITH ENHANCED ANTIMICROBIAL ACTIVITY IN RESPONSE TO LIGHT

(71) Applicants: International Business Machines Corporation, Armonk, NY (US); Agency for Science, Technology and Research, Connexis (SG)

(72) Inventors: Willy Chin, Singapore (SG); James L. Hedrick, Pleasanton, CA (US); Noah Frederick Fine Nathel, San Jose, CA (US); Victoria A. Piunova, Los Gatos, CA (US); Zhi Xiang Voo, Singapore (SG); Yi Yan Yang, Singapore (SG)

(73) Assignee: International Business Machines Corporation, Armonk, NY (US)

( * ) Notice: Subject to any disclaimer, the term of this patent is extended or adjusted under 35 U.S.C. 154(b) by 51 days.

(21) Appl. No.: 15/824,250

(22) Filed: Nov. 28, 2017

(65) Prior Publication Data
US 2019/0159456 A1 May 30, 2019

(51) Int. Cl.
| | |
|---|---|
| *A01N 47/06* | (2006.01) |
| *C08G 64/42* | (2006.01) |
| *C09D 5/14* | (2006.01) |
| *C09D 169/00* | (2006.01) |
| *C08G 64/16* | (2006.01) |
| *A01N 25/00* | (2006.01) |

(52) U.S. Cl.
CPC ............. *A01N 47/06* (2013.01); *A01N 25/00* (2013.01); *C08G 64/1641* (2013.01); *C08G 64/1658* (2013.01); *C08G 64/42* (2013.01); *C09D 5/14* (2013.01); *C09D 169/00* (2013.01)

(58) Field of Classification Search
CPC ....................................................... A01N 47/06
USPC ................................................. 528/370, 371
See application file for complete search history.

(56) References Cited

U.S. PATENT DOCUMENTS

| 8,765,098 B2 * | 7/2014 | Appel ............... A61K 49/0036 |
| | | 424/9.1 |
| 8,945,513 B2 | 2/2015 | Lee et al. |
| 2012/0251608 A1 | 10/2012 | Coady et al. |

(Continued)

FOREIGN PATENT DOCUMENTS

| CN | 103501769 | 1/2014 |
| CN | 104861172 A | 8/2015 |

OTHER PUBLICATIONS

Bing, Synthesis of Novel Photoactive Degradable Polymers with Potential in Biomedical Applications, The Hong Kong Polytechnic University, 2014.

(Continued)

*Primary Examiner* — Duc Truong
(74) *Attorney, Agent, or Firm* — Amin, Turocy & Watson, LLP

(57) ABSTRACT

Techniques regarding star polymers with enhanced antimicrobial functionality are provided. For example, a polymer is provided that can comprise a core that can have a singlet oxygen generator and that can generate a singlet oxygen species upon irradiation with light. The polymer can also comprise a plurality of polycarbonate arms covalently bonded to the core. The plurality of polycarbonate arms can be degradable and can comprise a cation. Further, the plurality of polycarbonate arms can have antimicrobial functionality.

25 Claims, 10 Drawing Sheets

(56) References Cited

U.S. PATENT DOCUMENTS

2014/0370064 A1    12/2014    Lee et al.
2015/0335760 A1    11/2015    Lee et al.
2016/0338356 A1    11/2016    Chin et al.

OTHER PUBLICATIONS

Vatansever, et al., Antimicrobial strategies centered around reactive oxygen species—bactericidal antibiotics, photodynamic therapy and beyond, FEMS Microbiol. Rev., May 16, 2013, pp. 955-989, vol. 37.

Oyinloye, et al., Reactive Oxygen Species, Apoptosis, Antimicrobial Peptides and Human Inflammatory Diseases, Pharmaceuticals 2015, pp. 151-175, vol. 8.

Kammerlander, et al., A clinical evaluation of the efficacy and safety of singlet oxygen in cleansing and disinfecting stagnating wounds, Journal of Wound Care, Apr. 2011, pp. 149-150, vol. 20, No. 4.

Stoller, et al., Oxygen Therapy for Patients With COPD Current Evidence and the Long-Term Oxygen Treatment Trial, CHEST Recent Advances in Chest Medicine, Jul. 2010, pp. 179-187, vol. 138(1).

Yang, et al., Broad-Spectrum Antimicrobial Star Polycarbonates Functionalized with Mannose for Targeting Bacteria Residing inside Immune Cells, Advanced Healthcare Materials, Mar. 2016, pp. 1-11.

Zhao, et al., Cationic Oligo(thiophene ethynylene) with Broad-Spectrum and High Antibacterial Efficiency under White Light and Specific Biocidal Activity against *S. aureus* in Dark, ACS Appl. Mater. Interfaces 2016, pp. 1019-1024, vol. 8.

Xing, et al., Conjugated Polymer/Porphyrin Complexes for Efficient Energy Transfer and Improving Light-Activated Antibacterial Activity, J. Am. Chem. Soc., Aug. 24, 2009, pp. 13117-13124, vol. 131.

Hynek, et al., Design of porphyrin-based conjugated microporous polymers with enhanced singlet oxygen productivity, RSC Adv., 2016, pp. 44279-44287, vol. 6.

Kralova, et al., Glycol Porphyrin Derivatives as Potent Photodynamic Inducers of Apoptosis in Tumor Cells, Journal of Medicinal chemistry, 2008, pp. 5964-5973, vol. 51.

Chan, et al., Tetra-n-butylammonium Fluoride as an Efficient Transesterification Catalyst for Functionalizing Cyclic Carbonates and Aliphatic Polycarbonates, ACS Macro Letteres, 2013, pp. 860-864, vol. 2.

Dove, et al. Thiourea-Based Bifunctional Organocatalysis: Supramolecular Recognition for Living Polymerization, J. Am. Chem. Soc., 2005, pp. 13798-13799, vol. 127.

Lohmeijer, et al., Guanidine and Amidine Organocatalysts for Ring-Opening Polymerization of Cyclic Esters, Macromolecules, 2006, pp. 8574-8583.

Chin, et al., Biodegradable Broad-Spectrum Antimicrobial Polycarbonates: Investigating the Role of Chemical Structure on Activity and Selectivity, Macromolecules, 2013, pp. 8797-8807, vol. 46.

Rumyantseva, et al., Improved Method of 5,10,15,20-Tetrakis(4-hydroxyphenyl)-porphyrins Synthesis, Macroheterocycles, 2013, pp. 59-61, vol. 6(1).

Fuhrhop, et al., Porphyrin Assemblies and Their Scaffolds, Langmuir, 2014, pp. 1-12, vol. 30(1).

Lee, et al., Nanogel Star Polymer Architectures: A Nanoparticle Platform for Modular Programmable Macromolecular Self-Assembly, Intercellular Transport, and Dual-Mode Cargo Delivery, Advanced Materials, 2011, pp. 4509-4515, vol. 23.

Appel, et al., Toward biodegradable nanogel star polymers via organocatalytic ROP, Chem. Commun, 2012, pp. 6163-6165, vol. 48.

List of IBM Patents or Applications Treated as Related.

International Search report for PCT/IB2018/058797 dated Feb. 11, 2019, 9 pages.

Non-Final Office Action received for U.S. Appl. No. 15/824,153 dated Sep. 10, 2019, 36 pages.

\* cited by examiner

902 — DISPOSING ON A SURFACE OF AN ARTICLE A FILM-FORMING COMPOSITION, THE FILM-FORMING COMPOSITION COMPRISING: A SOLVENT; AND A POLYMER COMPRISING GREATER THAN OR EQUAL TO 5 WEIGHT PERCENT OF THE FILM-FORMING COMPOSITION AND LESS THAN OR EQUAL TO 20 WEIGHT PERCENT OF THE FILM-FORMING COMPOSITION, THE POLYMER DISPERSED IN THE SOLVENT, AND THE POLYMER COMPRISING: A CORE HAVING A SINGLET OXYGEN GENERATOR AND THAT GENERATES A SINGLET OXYGEN SPECIES UPON IRRADIATION WITH LIGHT; AND A PLURALITY OF POLYCARBONATE ARMS COVALENTLY BONDED TO THE CORE, THE PLURALITY OF POLYCARBONATE ARMS BEING DEGRADABLE AND COMPRISING A CATION, WHEREIN THE PLURALITY OF POLYCARBONATE ARMS HAVE ANTIMICROBIAL FUNCTIONALITY

904 — REMOVING THE SOLVENT FROM THE SURFACE OF THE ARTICLE

906 — THERMAL AND/OR PHOTOCHEMICAL TREATING THE SURFACE OF THE ARTICLE TO FACILITATE CROSSLINKING BETWEEN THE ONE OR MORE STAR POLYMERS

1002 — CONTACTING A PATHOGEN WITH A POLYMER, THE POLYMER COMPRISING: A CORE HAVING A SINGLET OXYGEN GENERATOR AND THAT GENERATES A SINGLET OXYGEN SPECIES UPON IRRADIATION WITH LIGHT; AND A PLURALITY OF POLYCARBONATE ARMS COVALENTLY BONDED TO THE CORE, THE PLURALITY OF POLYCARBONATE ARMS BEING DEGRADABLE AND COMPRISING A CATION, WHEREIN THE PLURALITY OF POLYCARBONATE ARMS HAVE ANTIMICROBIAL FUNCTIONALITY, AND WHEREIN THE CONTACTING OF THE PATHOGEN WITH THE POLYMER ELECTROSTATICALLY DISRUPTS A MEMBRANE OF THE PATHOGEN

1004 — IRRADIATING THE ONE POLYMER WITH THE LIGHT, AND GENERATING THE SINGLET OXYGEN SPECIES VIA THE CORE

STAR POLYMERS WITH ENHANCED ANTIMICROBIAL ACTIVITY IN RESPONSE TO LIGHT

BACKGROUND

The subject disclosure relates to a star polymer with antimicrobial activity, and more specifically, to a star polymer that can exhibit enhanced antimicrobial activity in response to light.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, compositions and methods regarding star polymers that can exhibit enhanced antimicrobial activity in response to light are described.

According to an embodiment, a polymer is provided. The polymer can comprise a core that can have a singlet oxygen generator and that can generate a singlet oxygen species upon irradiation with light. The polymer can further comprise a plurality of polycarbonate arms covalently bonded to the core. The plurality of polycarbonate arms can be degradable and can comprise a cation. Further, the plurality of polycarbonate arms can have antimicrobial functionality.

According to another embodiment, a method is provided. The method can comprise forming a plurality of degradable polycarbonate arms by polymerizing a plurality of carbonates with a singlet oxygen generator core. The singlet oxygen generator core can generate a singlet oxygen species in response to being irradiated with light. The method can also comprise generating a cationic moiety by covalently bonding a functional group with a degradable polycarbonate arm from the plurality of degradable polycarbonate arms.

According to another embodiment, a film-forming composition is provided. The film-forming composition can comprise a solvent and a polymer. The polymer can comprise greater than or equal to 5 weight percent of the film-forming composition and less than or equal to 20 weight percent of the film-forming composition. Further, the polymer can be dispersed in the solvent. The polymer can also comprise a core that can have a singlet oxygen generator and that can generate a singlet oxygen species upon irradiation with light. The polymer can further comprise a plurality of polycarbonate arms covalently bonded to the core. The plurality of polycarbonate arms can be degradable and can comprise a cation. Moreover, the plurality of polycarbonate arms can have antimicrobial functionality.

According to another embodiment, a method of forming a surface treated article is provided. The method can comprise disposing on a surface of an article a film-forming composition. The film-forming composition can comprise a solvent and a polymer. The polymer can comprise greater than or equal to 5 weight percent of the film-forming composition and less than or equal to 20 weight percent of the film-forming composition. Further, the polymer can be dispersed in the solvent. The polymer can also comprise a core that can have a singlet oxygen generator and that can generate a singlet oxygen species upon irradiation with light. The polymer can further comprise a plurality of polycarbonate arms covalently bonded to the core. The plurality of polycarbonate arms can be degradable and can comprise a cation. Moreover, the plurality of polycarbonate arms can have antimicrobial functionality. The method can additionally comprise removing the solvent from the surface of the article.

According to another embodiment, a method of killing a pathogen is provided. The method can comprise contacting the pathogen with a polymer. The polymer can comprise a core that can have a singlet oxygen generator and that can generate a singlet oxygen species upon irradiation with light. The polymer can further comprise a plurality of polycarbonate arms covalently bonded to the core. The plurality of polycarbonate arms can be degradable and can comprise a cation. Further, the plurality of polycarbonate arms can have antimicrobial functionality. Moreover, the contacting of the pathogen with the polymer can electrostatically disrupt a membrane of the pathogen.

BRIEF DESCRIPTION OF THE DRAWINGS

FIG. 9 illustrates another flow diagram of an example, non-limiting method that can facilitate treating a surface of an article with a film-forming composition in accordance with one or more embodiments described herein.

FIG. 10 illustrates another flow diagram of an example, non-limiting method that can facilitate killing a pathogen through contact with a star polymer in accordance with one or more embodiments described herein.

DETAILED DESCRIPTION

Figure 1:
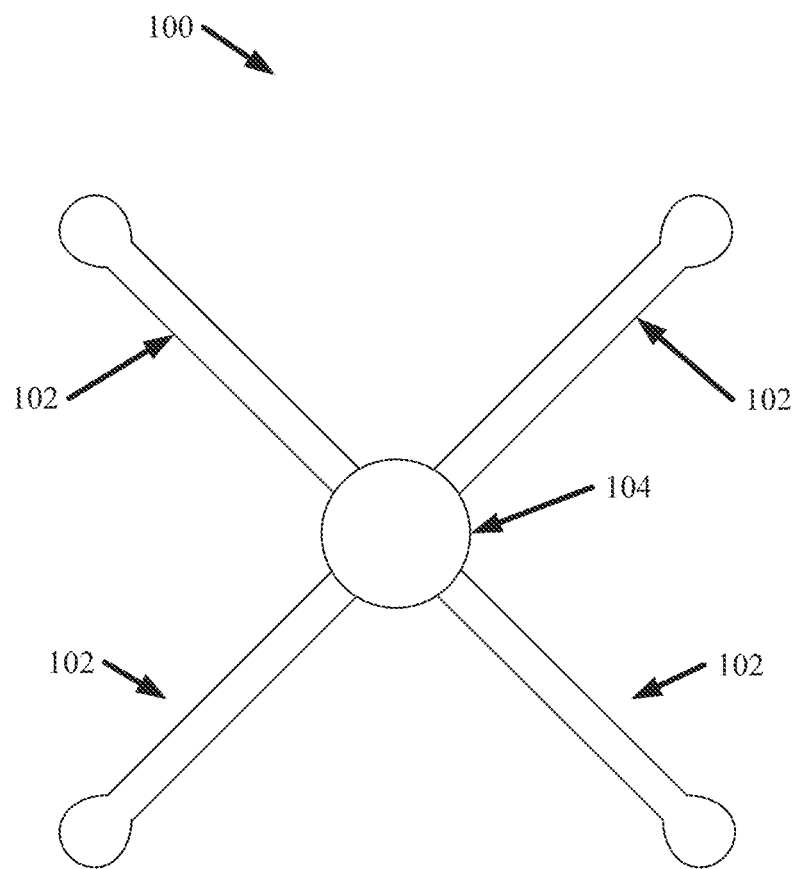
FIG. 1 illustrates a diagram of an example, non-limiting star polymer in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

In the recent decades, there has been a rise in antibiotic-resistant bacteria. Systemic overuse of broad-spectrum antibiotics has lead to a rise in multi-medication resistant bacteria commonly referred to as "superbugs." Further, biofilms can form on human tissue and implanted devices, leading to implant failure. The biofilms can be composed of bacteria embedded within a self-produced extracellular polymeric matrix. Thus, the biofilms can be difficult to penetrate, thereby rendering it difficult to kill the embedded bacteria.

As an alternative to conventional antibiotic techniques, reactive oxygen species (ROS) can exhibit strong antimicrobial, antiviral, and antifungal activity. Multiple reports claim that ROS can have high efficacy against various pathogens such as, but not limited to: Gram-positive bacteria, Gram-negative bacteria, fungi, and yeast. Further, ROS can be effective in cleansing and/or treating stagnate wounds and treating chronic obstructive pulmonary disease. Unfortunately, while ROS can be toxic to various pathogens, they can be equally as toxic against host cells. Additionally, conventional ROS can be unstable and exhibit undesirable burst releases.

Various embodiments described herein can provide compositions (e.g., film-forming compositions) and/or methods for the synthesis and/or use of antimicrobial star polymers with enhanced activity provided by light activated singlet oxygen generating functionalities. As used herein, the term "star polymer" can refer to a polymer having a plurality of arms, which can be crosslinked, branching from a discrete core. One or more embodiments can regard a polymer that can comprise a plurality of positively charged degradable polycarbonate arms covalently bonded to a singlet oxygen generating polymer core. In various embodiments, a film-forming composition can comprise the polymer compositions described herein. Further, one or embodiments can regard methods utilizing the polymer composition and/or film-forming composition to kill, and/or prevent contamination and/or growth of, various pathogens (e.g., Gram-positive bacteria, Gram-negative bacteria, fungi, and yeast) and/or surface treat various articles (e.g., food and/or medical packaging).

FIG. 1 illustrates a diagram of an example, non-limiting star polymer 100 in accordance with one or more embodiments described herein. The star polymer 100 can comprise a plurality of polycarbonate arms 102 covalently bonded to a singlet oxygen generator core 104. In various embodiments, the star polymer 100 can crosslink with one or more additional star polymers (e.g., star polymer 100) without the assistance of an additional chemical crosslinking agent and/or photochemical activation. The crosslinking can be chemical (e.g., covalent bonds), physical (e.g., hydrophobic bonding, chain entanglement, and/or ionic association), and/or a combination thereof. The plurality of polycarbonate arms 102 can be present in the star polymer 100 as homopolymers, random copolymers, block polymers, and/or a combination thereof.

In various embodiments, the star polymer 100 can comprise one or more functionalization sites that can be utilized to control chemical interactions that can facilitate antimicrobial and/or film-forming properties. For example, plurality of the polycarbonate arms 102 and/or the singlet oxygen generator core 104 can be capable of further chain growth.

Figure 2:
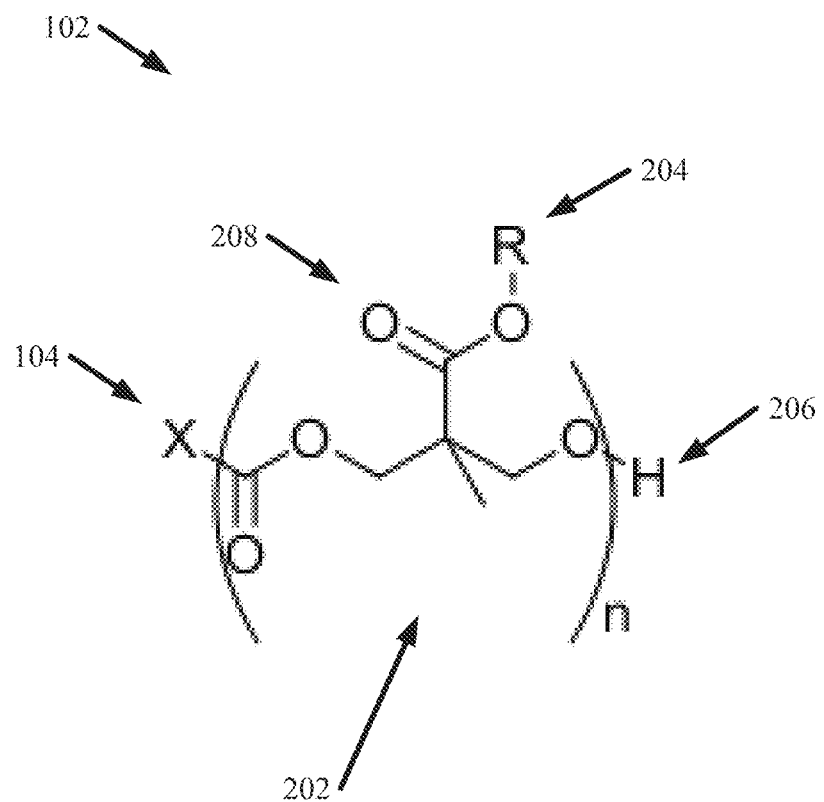
FIG. 2 illustrates a diagram of an example, non-limiting arm from a plurality of arms that can comprise a star polymer in accordance with one or more embodiments described herein.

FIG. 2 illustrates a drawing of an example, non-limiting polycarbonate arm 102 of the plurality of polycarbonate arms 102 that can comprise the star polymer 100. Repetitive description of like elements employed in other embodiments described herein is omitted for sake of brevity. In various embodiments, each polycarbonate arm 102 from the plurality of polycarbonate arms 102 can be characterized by the same structure. In one or more embodiments, one or more polycarbonate arms 102 of the star polymer 100 can exhibit the features described herein via a chemical structure different than one or more other polycarbonate arms 102 of the star polymer 100. Further, in some embodiments, the plurality of polycarbonate arms 102 can comprise four polycarbonate arms 102.

The polycarbonate arm 102 can have a positive charge when bonded to the singlet oxygen generator core 104. The polycarbonate arm 102 can comprise a molecular backbone 202 covalently bonded to the singlet oxygen generator core 104. Also, the polycarbonate arm 102 can comprise a cationic functional group 204 covalently bonded to the molecular backbone 202. In one or more embodiments, the polycarbonate arm 102 can further comprise a reactive end group 206 covalently bonded to the molecular backbone 202.

As shown in FIG. 2, "X" can represent the singlet oxygen generator core 104. Thus, FIG. 2 delineates that the polycarbonate arm's 102 molecular backbone 202 can be bonded to the singlet oxygen generator core 104. FIG. 2 illustrates an exemplary structure; however, alternate structures are also envisaged. Example chemical structures comprising the molecular backbone 202 can include, but are not limited to: alkyl structures, aryl structures, alkane structures, aldehyde structures, ether structures, ketone structures, ester structures, carboxyl structures, carbonyl structures, amine structures, amide structures, phosphide structures, phosphine structures, a combination thereof, and/or the like. One of ordinary skill in the art can recognize that the size of the molecular backbone 202 can vary depending of the desired function of the star polymer 100. For example, "n" can represent an integer great than or equal to 5 and less than or equal to 1000.

Additionally, the molecular backbone 202 can be covalently bonded to the cationic functional group 204 (e.g., illustrated in FIG. 2 as "R"). In one or more embodiments, the cationic functional group 204 can be bonded to the molecular backbone 202 via a first linkage group 208. FIG. 2 illustrates the first linkage group 208 having an ester structure; however other chemical structures are also envisaged. Example chemical structures for the first linkage group 208 can include, but are not limited to: alkyl structures, aryl structures, alkane structures, ether structures, carboxyl structures, ketone structures, ester structures, carboxyl structures, carbonyl structures, a combination thereof, and/or the like. In one or more embodiments, the first linkage group 208 can be a product of polymerization used to form the polycarbonate arm 102. In some embodiments, the first linkage group 208 can be a product of post-polymerization of the polycarbonate arm 102.

The cationic functional group 204 can comprise one or more nitrogen and/or phosphorus cations. Example nitrogen cations can include, but are not limited to: quaternary ammonium cations, protonated primary amine cations, protonated secondary amine cations, protonated tertiary amine cations, and/or imidazolium cations. Example, phosphorus cations can include, but are not limited to: quaternary phosphonium cations, protonated primary phosphine cations, protonated secondary phosphine cations, and/or protonated tertiary cations. Additionally, the cationic functional group 204 can comprise a hydrophobic group (e.g., an alkyl group and/or an aryl group) bonded to the one or more nitrogen cations and/or phosphorus cations. The nitrogen cations and/or phosphorus cations can be formed via protonation, alkylation, and/or quaternization.

In various embodiments, the polycarbonate arm 102 can further comprise a reactive end group 206 bonded to the molecular backbone 202. The reactive end group 206 can facilitate self-crosslinking of the star polymer 100 with another star polymer (e.g., another star polymer 100). The reactive end group 206 can comprise a halide ion located alpha to a carbonyl group and/or alpha to an aromatic ring. Example, halide ions include: fluoride, chloride, bromide, iodide, and astatide. Example carbonyl groups include, but are not limited to: alpha-halo ketones, alpha-halo esters, alpha-halo acids, alpha-halo amides, and/or a combination thereof. Example aromatic rings include, but are not limited to: phenyl, pyridinyl, and/or the like.

In various embodiments, the reactive end group 206 can be a product of polymerization used to form the polycarbonate arm 102. For example, the reactive end group 206 can comprise: an epoxide (e.g., from anionic polymerization), an alkoxyamine (e.g., from controlled radical polymerization), a dithioester (e.g., from reversible addition-fragmentation transfer polymerization), and/or a trithiocarbonate (e.g., from reversible addition-fragmentation transfer polymerization). In one or more embodiments, the reactive end group 206 can be prepared by chemically modifying the peripheral end of the polycarbonate arm 102. For example, the peripheral end of the polycarbonate arm 102 can be modified to produce a reactive end group 206 including, but not limited to: an azide, a thiol, an olefin, and/or an aryl substituted ketone.

Thus, in various embodiments, the polycarbonate arm 102 can be a degradable polycarbonate covalently bonded to a discrete singlet oxygen generator core 104, and the polycarbonate arm 102 can comprise a molecular backbone 202 bonded to a cationic functional group 204. The cationic functional group 204 can be positively charged (e.g., via one or more nitrogen and/or phosphorus cation) to facilitate antimicrobial functionality. Additionally, the cationic functional group 204 can comprise a hydrophobic group (e.g., bonded to the to one or more nitrogen and/or phosphorus cations), which can further enhance antimicrobial functionality. The cationic functional group 204 can be directly bonded to the molecular backbone 202, and/or the cationic functional group 204 can be bonded to the molecular backbone 202 via a first linkage group 208 (e.g., the first linkage group 208 can be formed as a product of the polymerization of the polycarbonate arm 102). Moreover, the molecular backbone 202 can be bonded to a reactive end group 206, which can facilitate crosslinkage of the star polymer 100 with another star polymer (e.g., star polymer 100).

The plurality of polycarbonate arms 102 can exhibit antimicrobial functionality through a lysis of pathogen cells. For example, a membrane of a subject pathogen cell can comprise a phospholipid bilayer. The phospholipid bilayer can comprise a plurality of molecules having hydrophilic heads and/or hydrophobic tails. Additionally, one or more of the plurality of membrane molecules can be negatively charged. The positive charge of the polycarbonate arm 102 (e.g., via the cationic functional group 204) can attract the star polymer 100 to the negatively charged membrane molecules and facilitate cleaving of said molecules from adjacent membrane molecules. The hydrophobicity of the polycarbonate arm 102 (e.g., via the cationic functional group 204) can further facilitate said cleaving as the hydrophobic group of the cationic functional group 204 integrates itself into the hydrophobic region of the membrane. Thus, the polycarbonate arm 102 can facilitate a lysis of the pathogen cell through electrostatic disruption and/or hydrophobic membrane integration. Example pathogen cells that can be subject to the antimicrobial effects of the polycarbonate arm 102 can include, but are not limited to: Gram-negative bacteria, Gram-positive bacteria, fungi and yeast.

Figure 3:
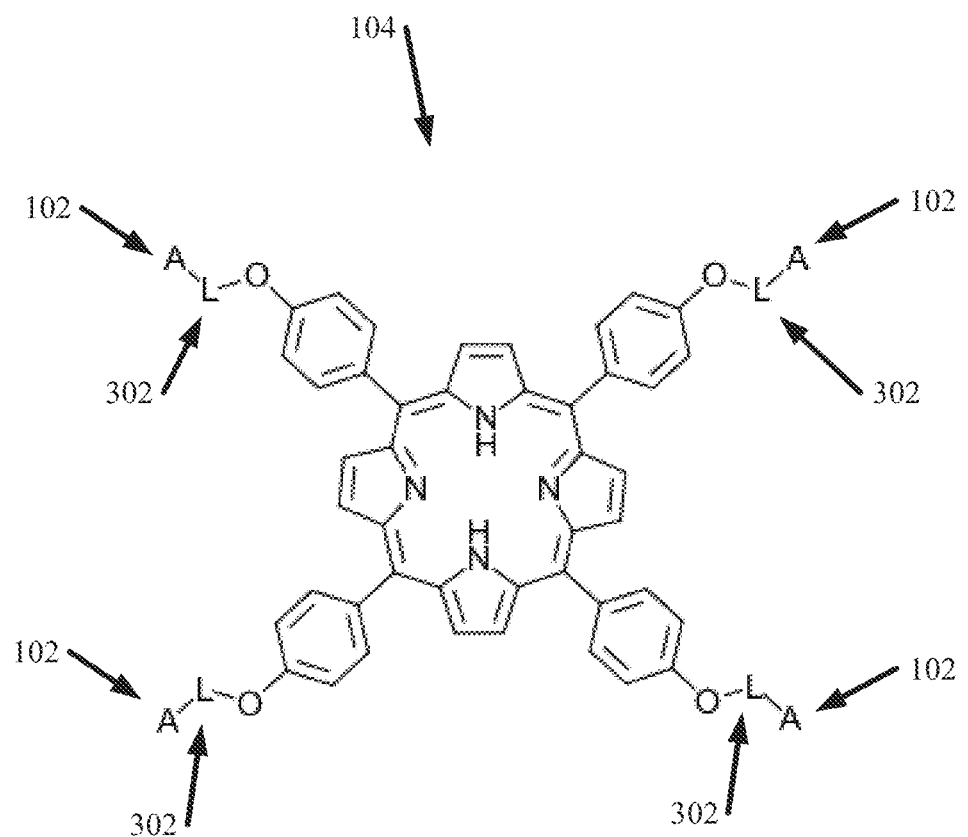
FIG. 3 illustrates a diagram of an example, non-limiting singlet oxygen generator core that can comprise a star polymer in accordance with one or more embodiments described herein.

FIG. 3 illustrates a diagram of an example, non-limiting singlet oxygen generator core 104 that can comprise the star polymer 100. Repetitive description of like elements employed in other embodiments described herein is omitted for sake of brevity. In one or more embodiments, the plurality of polycarbonate arms 102 can be crosslinked together and/or covalently bonded to the singlet oxygen generator core 104.

FIG. 3 shows the singlet oxygen generator core 104 with an exemplary chemical structure derived from a porphyrin; however, other chemical structures are also envisaged. For example, the singlet oxygen generator core 104 can have a chemical structure derived from a molecule selected from a group that can include, but is not limited to: a phthalocyanine, a phenothiazine, a xanthene, and/or a quinone. The singlet oxygen generator core 104 can comprise one or more second linkage groups 302 (e.g., represented by "L" in FIG. 3) that can facilitate bonding the plurality of polycarbonate arms 102 (e.g., represented by "A" in FIG. 3) to the singlet oxygen generator core 104. For example, the second linkage group 302 can be derived from an alcohol and/or an ether (e.g., an alcohol comprising a halide). In one or more embodiments, a periphery of the second linkage group 302 can comprise an oxygen atom (e.g., derived from a hydroxyl group) such that a polycarbonate structure is formed by the bonding of an arm 102 and a second linkage group 302.

Upon being irradiated with light, the singlet oxygen generator core 104 can generate one or more singlet oxygen species, which can enhance antimicrobial functionality of the star polymer 100. Thus, the star polymer 100 can exhibit enhanced anti-microbial functionality on-demand. For example, the singlet oxygen generator core 104 can generate one or more singlet oxygen species in response to light having a wavelength greater than or equal to 10 nanometers (nm) and less than or equal to 750 nm.

Figure 4:
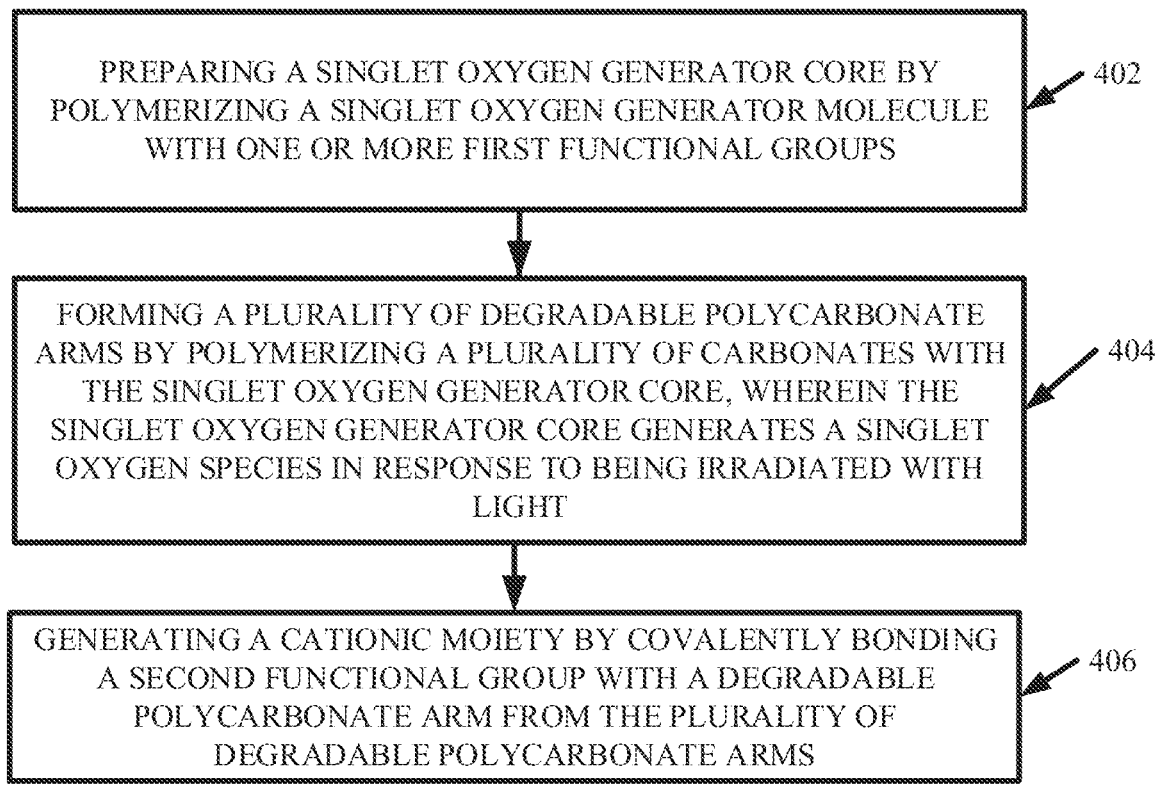
FIG. 4 illustrates a flow diagram of an example, non-limiting method that can facilitate generation of a star polymer in accordance with one or more embodiments described herein.

FIG. 4 illustrates a flow diagram of an example, non-limiting method 400 that can facilitate generating the star polymer 100 in accordance with in one or more embodiments described herein. Repetitive description of like elements employed in other embodiments described herein is omitted for sake of brevity.

At 402, the method 400 can comprise preparing the singlet oxygen generator core 104 by polymerizing a singlet oxygen generator molecule with a first functional group. For example, the singlet oxygen generator molecule and the first functional group can be mixed together in a solvent to form a solution. The solution can then be heated (e.g., to a temperature greater than or equal to 100 degrees Celsius (° C.) and less than or equal to 200° C.). Further, the solution can be agitated (e.g., stirred) for a defined period of time (e.g., greater than or equal to 12 hours and less than or equal to 48 hours). Also, the solution can optionally be agitated under nitrogen gas. The singlet oxygen generator core 104 can form as a precipitate of the solution.

Preparing the singlet oxygen generator core 104 can comprise bonding one or more first functional groups to a singlet oxygen generating molecule. The singlet oxygen generating molecule can generate one or more singlet oxygen species in response to being irradiated with light (e.g., light having a wavelength greater than or equal to 10 nm and less than or equal to 750 nm). Example singlet oxygen generating molecules can include, but are not limited to: a porphyrin, a phthalocyanine, a phenothiazine, a xanthene, a quinone, and/or the like. Example first functional groups can comprise alcohol groups, carboxyl groups, ester groups, and/or one or more halides. Further, the one or more first functional groups can facilitate a bonding of the plurality of polycarbonate arms 102 to the singlet oxygen generating molecule and later become the second linkage group 302 when said bonding occurs. For example, one or more first functional groups can comprise an alcohol group such that the preparing at 402 results in a singlet oxygen generator core 104 comprising one or more hydroxyl groups that can facilitate the polymerization of a plurality of polycarbonate arms 102.

At 404, the method 400 can comprise forming a plurality of degradable polycarbonate arms 102 by polymerizing a plurality of carbonates with the prepared singlet oxygen generator core 104 (e.g., in the presence of an organocatylst). For example, the plurality of carbonates and the prepared singlet oxygen generator core 104 can be mixed with one or more solvents and/or one or more organocatylsts to form a solution. The solution can be agitated (e.g., stirred) at room temperature ("RT") for a defined period of time (e.g., greater than or equal to 30 minutes and less than or equal to 120 minutes).

The polymerization at 404 can covalently bond a plurality of carbonates together to form a one or more degradable polycarbonate structures, and/or the polymerization can covalently bond the one or more degradable polycarbonate structures to the prepared singlet oxygen generator core 104. Further, one or more of the carbonates and/or one or more of the polycarbonate structures can comprise a second functional group. The second functional group can facilitate later generation of the cationic functional group 204. For example, the second functional group can comprise an alkyl halide.

Covalently bonding the plurality of carbonates together to form the polycarbonate structure can form the molecular backbone 202. Further, one or more of the polycarbonate structures can be covalently bonded to the first functional group to facilitate bonding to the prepared singlet oxygen generator core 104, whereupon the first functional group can become the second linkage group 302.

For example, the one or more of the plurality of carbonates can be cyclic carbonates, and the polymerization at 404 can comprise ring-opening polymerization (ROP) of the cyclic carbonates to form a polycarbonate structure (e.g., molecular backbone 202). The one or more carbonates can have a structure characterized by formula 1:

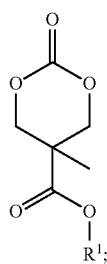

wherein $R^1$ can represent the second functional group. Thus, the ROP can form a polycarbonate structure characterized by formula 2:

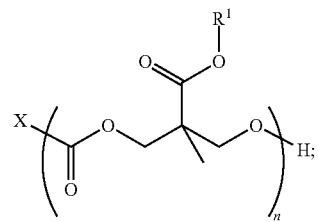

wherein $R^1$ can represent the second functional group, "X" can represent a bond to the singlet oxygen generator core 104, and "n" can represent an integer greater than or equal to 5 and less than or equal to 1000. For instance, the second functional group can be 4-methylbenzyl chloride, thereby rendering one or more carbonates of 2-oxo-5-methyl-1,3-dioxane-5-carboxylic acid 4-(chloromethyl)benzyl ester ("MTC-OBnCl"). Whereupon, the polymerization at 404 can comprise a ROP of the MTC-OBnCl carbonates to form a polycarbonate structure characterized by formula 3:

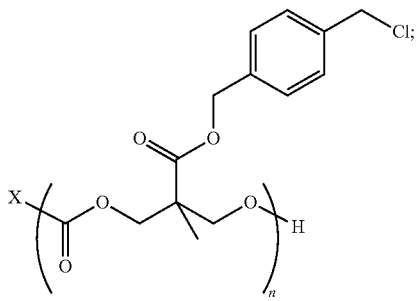

wherein "X" can represent a bond to the singlet oxygen generator core 104, and "n" can represent an integer greater than or equal to 5 and less than or equal to 1000. In the examples described above, the first linkage group 208 is formed as a result of the polymerization at 404; however, as described herein, the first linkage group 208 can also be formed post said polymerization at 404. Similarly, in one or more embodiments, the second functional group can be covalently bonded to one or more of the carbonates prior to the polymerization at 404; while in some embodiments the second functional group can be covalently bonded to the polycarbonate structure post polymerization at 404.

At 406, the method 400 can comprise generating a cationic moiety (e.g. the cationic functional group 204) by covalently bonding a third functional group with a degradable polycarbonate arm 102 from the plurality of degradable polycarbonate arms 102 (e.g., polycarbonate structures that can be characterized by molecular backbone 202), thereby forming the star polymer 100. For example, the intermediate structure formed at 404 can be mixed with the third functional group in a solvent at RT for a defined period of time (e.g., greater than or equal to one day and less than or equal to three days). Also, the solvent can comprise an acetyl group.

The third functional group can comprise an amine group, an imidazole (e.g., a structure comprising an imidazole ring) and/or a phosphine group. Further, generating the cationic moiety (e.g., cationic functional group 204) at 406 can comprise covalently bonding the third functional group to a second functional group of a polycarbonate structure formed at 404. For example, the third functional group can be covalently bonded to the second functional group through alkylation and/or quaternization. The third functional group can be covalently bonded to the second functional group in the presence of an acetyl group to generate the cationic moiety (e.g., the cationic functional group 204).

Thus, in various embodiments, the method 400 can comprise preparing (e.g., at 402) a singlet oxygen generator core 104 by polymerizing a singlet oxygen generator molecule (e.g., a porphyrin, a phthalocyanine, a phenothiazine, a xanthene, and/or a quinone) with one or more first functional groups (e.g., an alcohol group). The singlet oxygen generator core 104 can generate a singlet oxygen species in response to light (e.g., light having a wavelength greater than or equal to 10 nm and less than or equal to 750 nm). Also, the method 400 can comprise forming (e.g., at 404) a plurality of degradable polycarbonate structures (e.g., characterized by molecular backbone 202) by polymerizing a plurality of carbonates with the singlet oxygen generator core 104 (e.g., in the presence of an organocatalyst). The polymerization can covalently bond the plurality of carbonates together to form the one or more polycarbonate structures (e.g., characterized by the molecular backbone 202 of a plurality of degradable polycarbonate arms 102). The polymerization can also form one or more second functional groups bonded to the one or more polycarbonate structures, wherein the second functional groups (e.g., an alkyl halide) can facilitate generation of one or more cationic moieties. Further, the polymerization can covalently bond the one or more polycarbonate structures to the singlet oxygen generator core 104 via the first functional group, whereupon the first functional group can thereby transform into a linkage group (e.g., second linkage group 302). Additionally, the method 400 can comprise generating (e.g., at 406) one or more cation moieties (e.g., cationic functional group 204) by covalently bonding one or more third functional groups (e.g., an amine group, an imidazole group, and/or a phosphine group) with one or more of the polycarbonate structures to form a plurality of positively charged degradable polycarbonates (e.g., polycarbonate arms 102), and thereby a star polymer (e.g., star polymer 100). Generating the one or more cationic moieties can comprise an alkylation and/or quaternization of the third functional group with the second functional group to generate the one or more cationic moieties (e.g., cation functional group 204), whereupon the second functional group can thereby transform into another linkage group (e.g., first linkage group 208). The one or more cationic moieties can comprise a nitrogen cation (e.g., a protonated primary amine cation, a protonated secondary amine cation, a protonated tertiary amine cation, a quaternary ammonium cation, and/or an imidazolium cation) and/or a phosphorus cation (e.g., a protonated primary phosphine cation, a protonated secondary phosphine cation, a protonated tertiary phosphine cation, a quaternary phosphonium cation). Moreover, the one or more of the generated cation moieties can further comprise a hydrophobic functional group (e.g., bonded to the nitrogen cation and/or the phosphorus cation). In addition, the polymerized degradable polycarbonates (e.g., polycarbonate arms 102) can comprise a reactive functional group (e.g., reactive end group 206) to facilitate crosslinkage of the star polymer (e.g., star polymer 100) with another star polymer (e.g., another star polymer 100).

Figure 5:
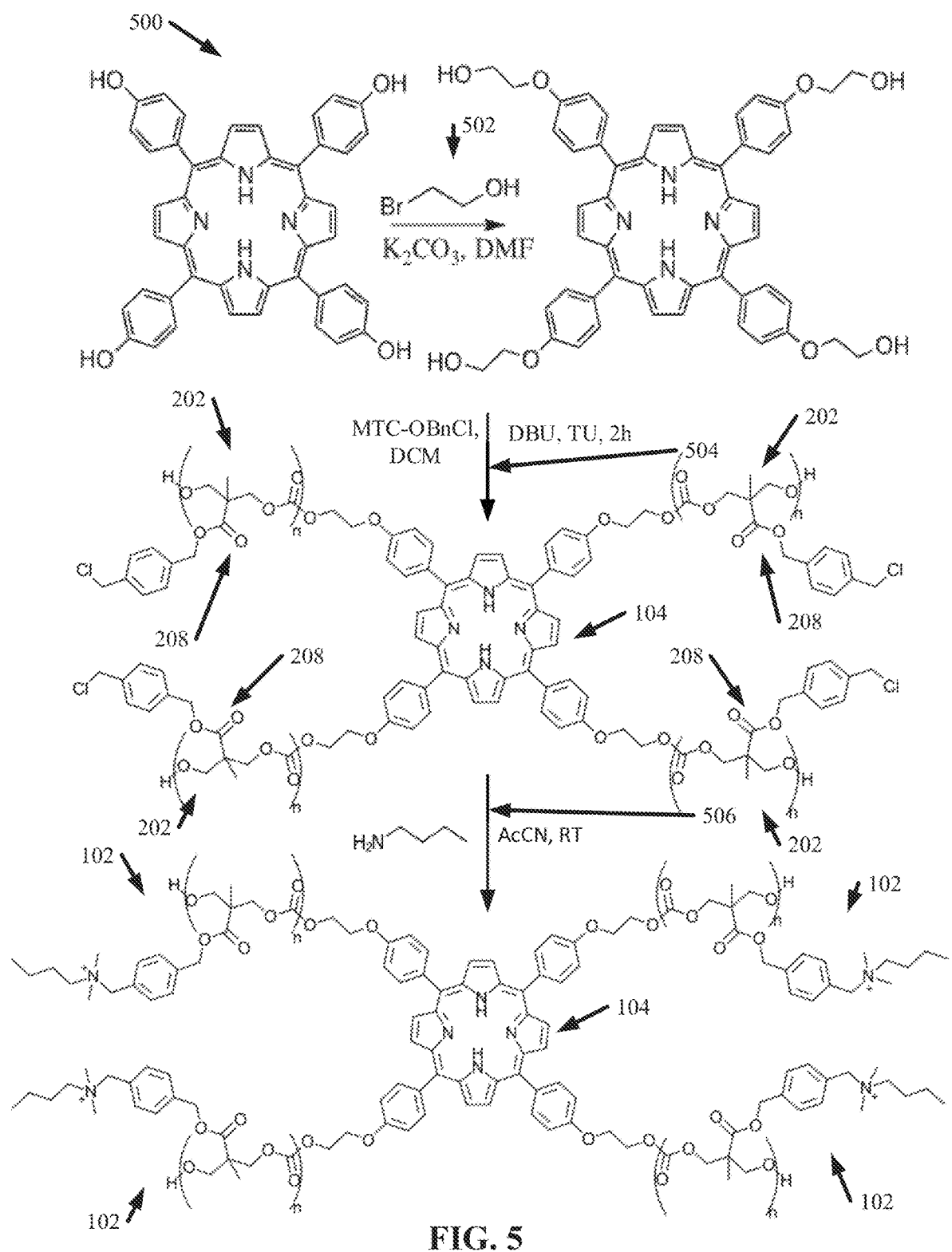
FIG. 5 illustrates a diagram of an example, non-limiting scheme that can facilitate generation of a star polymer in accordance with one or more embodiments described herein.

FIG. 5 illustrates a diagram of an example, non-limiting scheme 500 that can exemplify the formation of a star polymer 100 in accordance with one or more embodiments described herein (e.g., method 400). Repetitive description of like elements employed in other embodiments described herein is omitted for sake of brevity.

At 502, the scheme 500 can depict a preparation of the singlet oxygen generator core 104 (e.g., in accordance with 402 of method 400). For example, 5,10,15,20-Tetrakis(4hydroxyphenyl)porphyrin ("TPP") can be polymerized with 2-bromoethanol in potassium carbonate and dimethylformamide ("DMF") to produce hydroxyl-TPP. Here, the ethanol can serve as the first functional group, thereby providing a hydroxyl group to facilitate covalent bonding of one or more polycarbonate structures (e.g., molecular backbone 202).

At 504, the scheme 500 can depict forming the plurality of degradable polycarbonate structures (e.g., characterized by molecular backbone 202) by polymerizing a plurality of carbonates with the singlet oxygen generator core 104 in an organocatlyst (e.g., in accordance with 404 of method 400). For example, the hydroxyl-TPP can be polymerized with a plurality of MTC-OBnCl carbonates in the presence of dichloromethane ("DCM"), 1,8-diazabicyclo[5.4.0]undec-7-ene ("DBU"), and 1-1-[3,5-bis(trifluoromethyl)-phenyl]-3-cyclohexyl-2-thiourea ("TU") for defined period of time (e.g., two hours). As the plurality of carbonates polymerize together, they can form one or more molecular backbones 202. Also, as the polycarbonate structures polymerize, they can covalently bond to one or more of the hydroxyl groups of the hydroxyl-TPP; thereby transforming the one or more first functional groups into the one or more second linkage groups 302. Further, the 4-methylbenzyl chloride functional group of the carbonates can serve as the second functional group, which can facilitate generating the cationic moiety. As depicted in FIG. 5, the polymerization at 504 can produce an intermediate structure in the scheme 500.

At 506, the scheme 500 can depict a generation of one or more cationic moieties (e.g., cationic functional group 204) by covalently bonding one or more third functional groups with one or more of the degradable polycarbonate structures (e.g., in accordance with 406 of method 400). For example, the intermediate structure can be mixed with dimethylbutylamine in acetonitrile ("AcCN") to form a solution. The solution can be agitated (e.g., stirred) at RT for a defined period of time (e.g., greater than or equal to 1 hour and less than or equal to 6 hours). Here, the dimethylbutylamine can serve as the third functional group, and quaternization of the dimethylbutylamine can bond the dimethylbutylamine to the second functional group and form a nitrogen cation (e.g., a quaternary ammonium cation), thereby installing a positive charge to the plurality of polycarbonate arms 102. Subsequently, the solvent can be removed from the solution and a dialysis can be performed to retrieve the product (e.g., the star polymer 100). For example, the dialysis can be carried out over a defined period of time (e.g., greater than or equal to one day and less than or equal to three days) at RT using 1:1 alcohol and acetonitrile.

Figure 6:
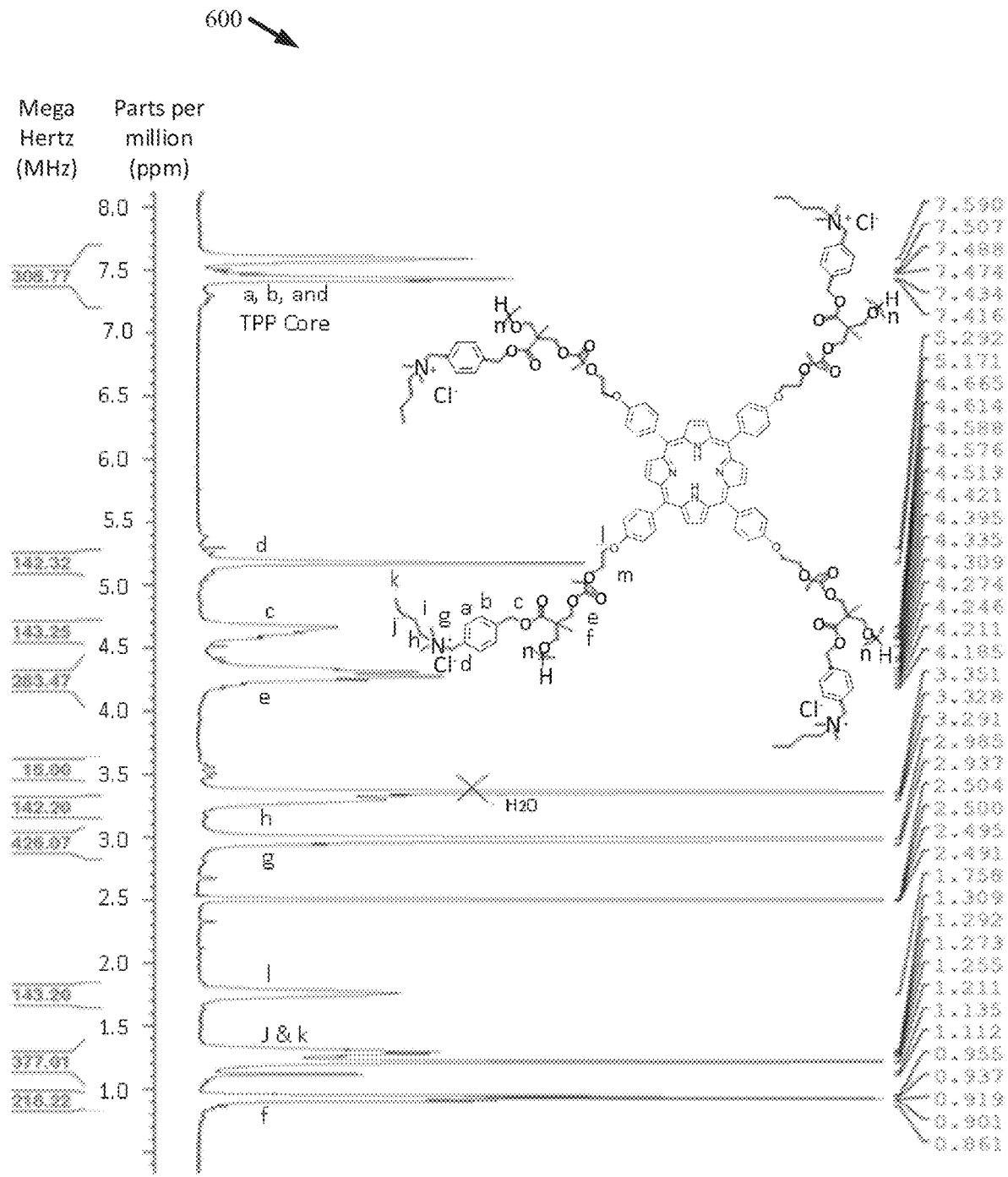
FIG. 6 illustrates a diagram of an example, non-limiting chart that can demonstrate a composition of a star polymer generated in accordance with one or more embodiments described herein.

FIG. 6 illustrates a diagram of an example, non-limiting chart 600 that can confirm the structure of a star polymer 100 created by scheme 500 in accordance with one or more embodiments described herein (e.g., method 400). Repetitive description of like elements employed in other embodiments described herein is omitted for sake of brevity.

In one or more embodiments, a star polymer 100 can be generated in accordance with method 400 and/or scheme 500. For example, 200 milligrams (mg) of 0.029 millimole (mmol) TPP can be charged in a 50 milliliter (mL) flask equipped with a stir bar with 501 mg of 3.63 mmol potassium carbonate and 8.61 microliters (μL) of 0.044 mmol 15-crown-5 in 25 mL of DMF. The reaction mixture can be stirred for 15 minutes at RT before 185 μL of 2.61 mmol 2-bromoethanol can be added in a dropwise fashion. Subsequently, the mixture can be heated at 140° C. and stirred under nitrogen for 24 hours. After the reaction has proceeded completely, the solvent can be removed under vacuum and the residual solids can be dissolved in 25 mL of tetrahydrofuran ("THF"). An organic layer can then be extracted twice with 15 mL of water, once with 15 mL of brine, and dried over sodium sulfate. Subsequently, the solvent can be removed and the crude product can be re-dissolved in 5 mL of THF. Next, a precipitation in cold diethyl ether can follow. The precipitate can be filtered and placed under vacuum for 18 hours, whereupon the final product can be hydroxyl-TPP.

Further, 4.3 mg of 0.005 mmol hydroxyl-TPP and 150 mg of 0.5 mmol MTC-OBnCl can be placed in a 20 mL glass vial equipped with a stir bar. Additionally, DCM can be added to the glass vial to ensure all solids are dissolved. The monomer concentration can be calibrated to 2 moles per liter (M). After which, 3.7 μL of 0.025 mmol DBU and 9.3 mg of 0.025 mmol TU can be added to initiate polymerization. The mixture can be stirred at RT for 1.5 hours. Next, 30 mg of benzoic acid can be added to the mixture to quench the reaction. Subsequently, the polymer intermediate can be purified via precipitation in cold diethyl ether and dried under vacuum.

The polymer intermediate can then be dissolved in 2 mL of acetonitrile and subsequently, quaternized with 750 μL of dimethylbutylamine at RT with stirring for 4.5 hours. The solvent can be removed under vacuum and the quaternized polymer can be dissolved in 4 mL of isopropanol and acetonitrile mixture having a 1:1 ratio. Further, the solution can be placed within a dialysis bag of 1000 molecular weight cut-off. Dialysis can be carried for two days at RT using 1:1 isopropanol and acetonitrile. Lastly, the solvents can be removed and the polymer lyophilized to obtain a star polymer 100 product.

The chemical structure of the star polymer 100 product can then be analyzed using proton nuclear magnetic resonance ($^1$H NMR) to generate chart 600. Chart 600 illustrates that the polymer generated in accordance with one or more embodiments described herein (e.g., method 400 and/or scheme 500) can exhibit the features of a star polymer 100 described herein. For example, $^1$H NMR spectra can be recorded on a Bruker Avance 2000 spectrometer operating at 400 mega hertz (MHz) (proton) and can be referenced to an internal solvent (e.g., $^1$H=7.26 parts per million (ppm)). The $^1$H NMR spectra can be recorded at RT using standard Bruker library pulse programs. Further, analytical permeation chromatography (GPC) and/or dynamic light scattering (LS) measurements can be conducted.

Figure 7:
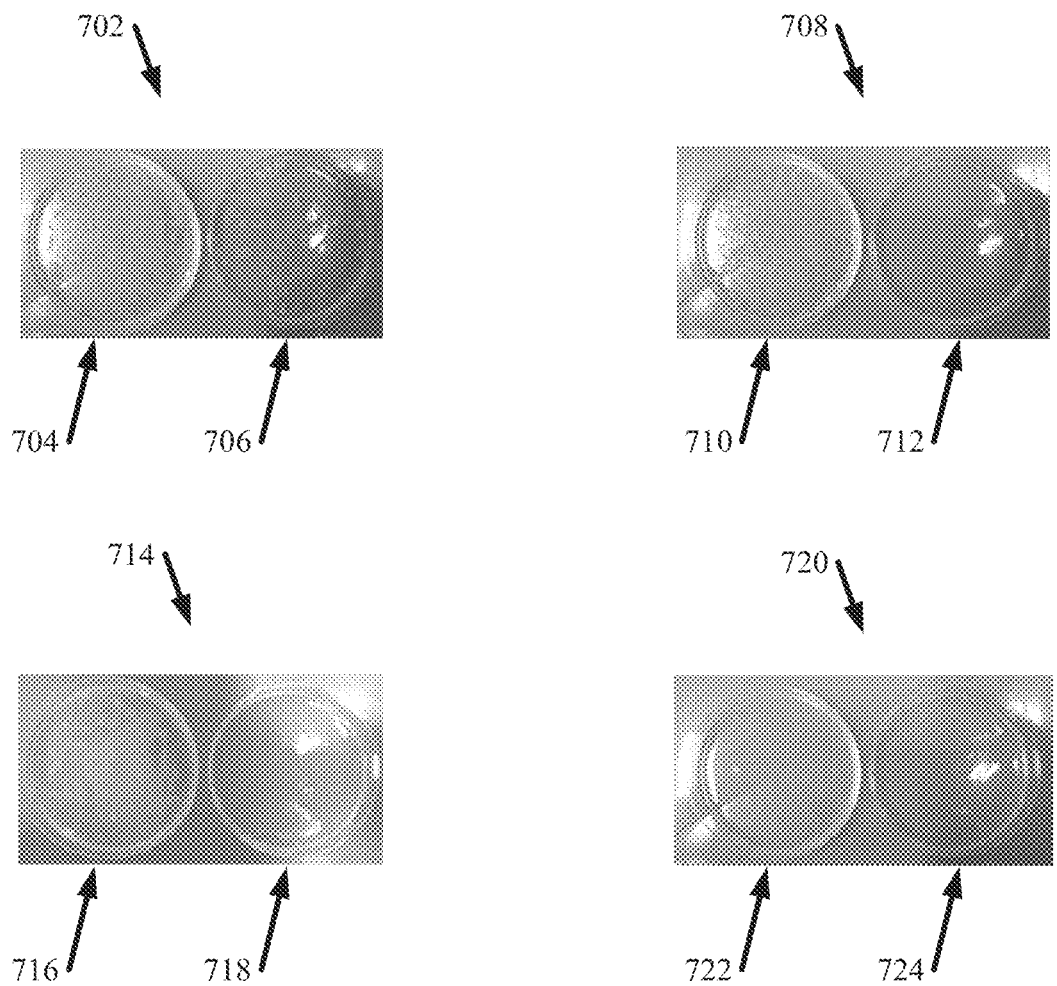
FIG. 7 illustrates four photos of example, non-limiting agar plates that can demonstrate the antimicrobial efficacy of a star polymer in accordance with one or more embodiments described herein.

FIG. 7 illustrates eight photos of example, non-limiting agar plates used to demonstrate the antimicrobial efficacy of the star polymer 100. Repetitive description of like elements employed in other embodiments described herein is omitted for sake of brevity. For example, the eight photos are illustrated in pairs to demonstrate the effect of irradiating the star polymer 100 with light at varying concentrations. Each of the agar plates shown in FIG. 7 comprise a growth solution, a bacterial culture of *Pseudomonas aeruginosa*, and a concentration of the star polymer 100 formed in accordance with method 400 and/or scheme 500 and analyzed by chart 600.

The first photo pair 702 can regard agar plates comprising the star polymer 100 at a 16 micrograms per milliliter (μg/mL) concentration. The first agar plate 704 can depict the antimicrobial functionality of the star polymer 100 at 16 μg/mL, wherein the star polymer 100 is not irradiated with light. The second agar plate 706 can depict the antimicrobial functionality of the star polymer 100 at 16 μg/mL, wherein the star polymer 100 is irradiated with light.

The second photo pair 708 can regard agar plates comprising the star polymer 100 at a 31 micrograms per milliliter (μg/mL) concentration. The third agar plate 710 can depict the antimicrobial functionality of the star polymer 100 at 31 μg/mL, wherein the star polymer 100 is not irradiated with light. The fourth agar plate 712 can depict the antimicrobial functionality of the star polymer 100 at 31 μg/mL, wherein the star polymer 100 is irradiated with light.

The third photo pair 714 can regard agar plates comprising the star polymer 100 at a 63 micrograms per milliliter (μg/mL) concentration. The fifth agar plate 716 can depict the antimicrobial functionality of the star polymer 100 at 63 μg/mL, wherein the star polymer 100 is not irradiated with light. The sixth agar plate 718 can depict the antimicrobial functionality of the star polymer 100 at 63 μg/mL, wherein the star polymer 100 is irradiated with light.

The fourth photo pair 720 can regard agar plates comprising the star polymer 100 at a 125 micrograms per milliliter (μg/mL) concentration. The seventh agar plate 722 can depict the antimicrobial functionality of the star polymer 100 at 125 μg/mL, wherein the star polymer 100 is not irradiated with light. The eighth agar plate 724 can depict the antimicrobial functionality of the star polymer 100 at 125 μg/mL, wherein the star polymer 100 is irradiated with light.

Figure 8:
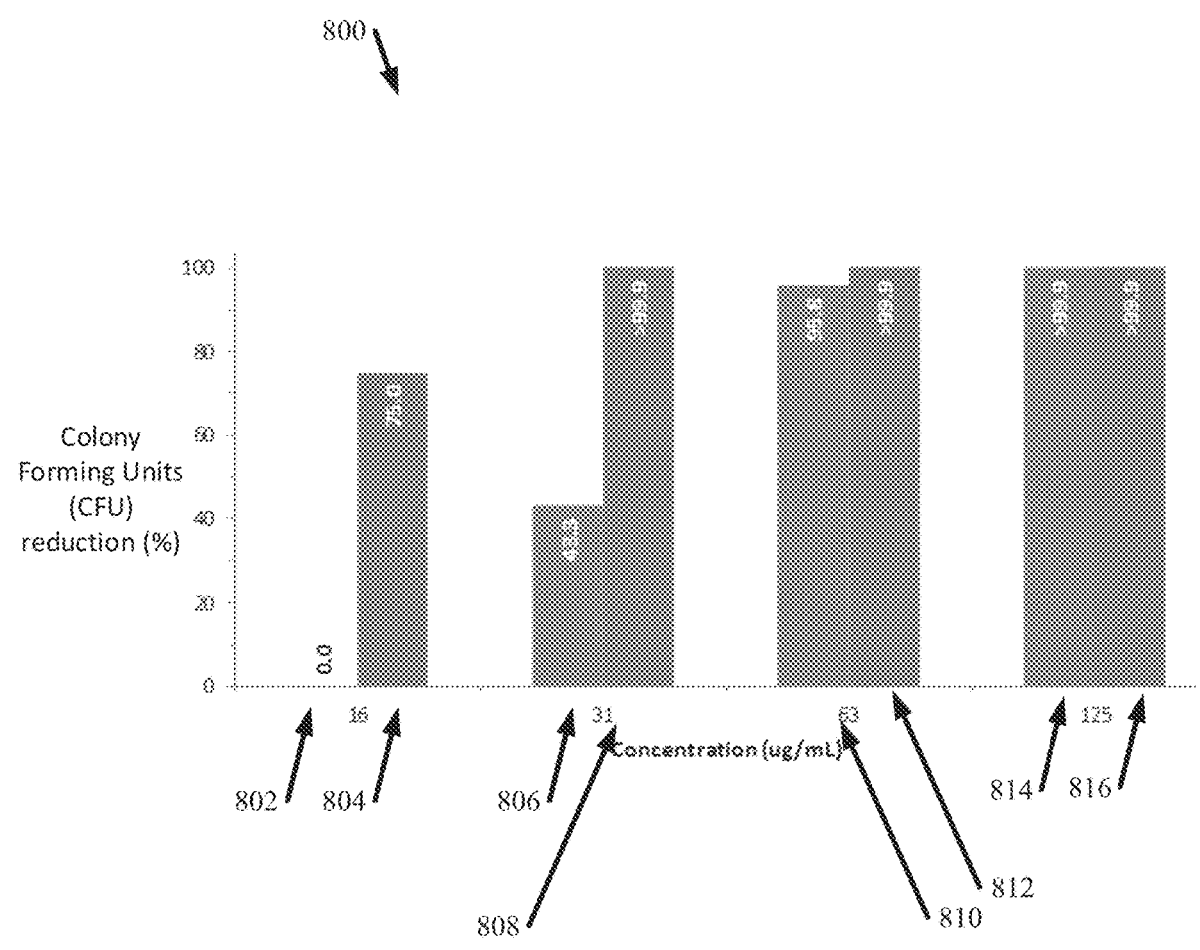
FIG. 8 illustrates a diagram of an example, non-limiting bar graph that can demonstrate the antimicrobial efficacy of a star polymer in accordance with one or more embodiments described herein.

FIG. 8 illustrates a diagram of an example, non-limiting bar graph 800 that analytically exemplifies the antimicrobial effect of each of the agar plates depicted in FIG. 7. Repetitive description of like elements employed in other embodiments described herein is omitted for sake of brevity. The first bar 802 can regard the first agar plate 704; the second bar 804 can regard the second agar plate 706; the third bar 806 can regard the third agar plate 710; the fourth bar 808 can regard the fourth agar plate 712; the fifth bar 810 can regard the fifth agar plate 716; the sixth bar 812 can regard the sixth agar plate 718; seventh bar 814 can regard the seventh agar plate 722; and the eighth bar 816 can regard the eighth agar plate 724.

The visual appearance of antimicrobial activity depicted in FIG. 7 and the analytics presented in bar graph 800 provide strong evidence that a singlet oxygen generator core 104 upon irradiation with light (e.g., visible light and/or ultraviolet light) can greatly enhance antimicrobial activity of the star polymer 100. While the plurality of polycarbonate arms 102 exhibit antimicrobial functionality (e.g., as evident by the third agar plate 710, the fifth agar plate 716, the seventh agar plate 722, the third bar 806, the fifth bar 810, and the seventh bar 814) independently, the additional antimicrobial activity facilitated by the singlet oxygen generator core 104 can significantly enhance the antimicrobial efficacy (e.g., as evident by the second agar plate 706, the fourth agar plate 712, the sixth agar plate 718, the eighth agar plate 724, the second bar 804, the fourth bar 808, the sixth bar 812, and the eighth bar 816). Moreover, the presence of polymeric chains around the singlet oxygen generator core 104 can extend the circulation time and minimizes toxicity of the otherwise cytotoxic star polymer 100.

In various embodiments, the star polymer 100 described herein can be used to create a film-forming composition to facilitate surface treatment of various articles such as, but not limited to, food packages and/or medical devices. The film-forming composition can comprise a solvent and one or more of the star polymers 100 described herein, wherein the one or more star polymers 100 can be dispersed in the solvent. In various embodiments, the star polymer 100 can comprise greater than or equal to 0.1 weight percent of the film-forming composition and less than or equal to 50 weight percent of the film-forming composition. In some embodiments, the star polymer 100 can comprise greater than or equal to 5 weight percent of the film-forming composition and less than or equal to 20 weight percent of the film-forming composition.

Thus, in one or more embodiments a film-forming composition can comprise a solvent (e.g., water and/or an organic solvent) and a star polymer (e.g., star polymer 100). The star polymer (e.g., star polymer 100) can comprise greater than or equal to 5 weight percent of the film-forming composition and less than or equal to 20 weight percent of the film-forming composition. The star polymer (e.g., star polymer 100) can be dispersed in the solvent. Also, the star polymer (e.g., star polymer 100) can comprise a singlet oxygen generator core 104 and a plurality of degradable polycarbonate arms 102. The singlet oxygen generator core 104 can be derived from a single oxygen generator molecule (e.g., a porphyrin, a phthalocyanine, a phenothiazine, a xanthene, and/or a quinone). Further, the singlet oxygen generator core 104 can comprise one or more linkage groups (e.g., second linkage group 302) to facilitate bonding of the degradable polycarbonate arms 102. The singlet oxygen generator core 104 can generate one or more singlet oxygen species in response to being irradiated with light (e.g., light having a wavelength greater than or equal to 10 nm and less than or equal to 750 nm). The plurality of degradable polycarbonate arms 102 (e.g., four polycarbonate arms 102) can be covalently bonded to the singlet oxygen generator core 104 (e.g., via the second linkage group 302). The plurality of polycarbonate arms 102 can comprise a cationic functional group 204 covalently bonded to a molecular backbone 202 (e.g., via the first linkage group 208). The cationic functional group 204 can comprise a nitrogen cation (e.g., a protonated primary amine cation, a protonated secondary amine cation, a protonated tertiary amine cation, a quaternary ammonium cation, and/or an imidazolium cation) and/or a phosphorus cation (e.g., a protonated primary phosphine cation, a protonated secondary phosphine cation, a protonated tertiary phosphine cation, a quaternary phosphonium cation). Further, the cationic functional group 204 can comprise a hydrophobic group (e.g., bonded to the cation). Additionally, the polycarbonate arms 102 can comprise a reactive end group 206 to facilitate a crosslinkage between the star polymer (e.g., star polymer 100) and another star polymer (e.g., another star polymer 100). The film-forming composition can be toxic to a pathogen (e.g., a Gram-negative bacteria, a Gram-positive bacteria, fungi, and/or yeast).

In one or more embodiments, the film-forming composition can additionally comprise one or more additives to increase efficacy. Example additives can include, but are not limited to: an antimicrobial metal (e.g., nanoparticles of silver, gold, and/or copper), ceramic nanoparticles (e.g., titanium dioxide and/or zinc oxide), antimicrobial metal salts, a pigment, a surfactant, a thickener, an accelerator to speed crosslinking between star polymers 100, a combination thereof, and/or the like.

In various embodiments, the star polymers 100 do not readily crosslink with other star polymers (e.g., other star polymers 100) in the presence of the solvent; rather, said crosslinking is performed upon removal of the solvent. Thus, the film-forming composition can exhibit a stable shelf life. Example solvents include, but are not limited to: water, an organic solvent, a combination thereof, and/or the like.

FIG. 9 illustrates a flow diagram of an example, non-limiting method 900 for forming a surface treated article. Repetitive description of like elements employed in other embodiments described herein is omitted for sake of brevity. Example articles that can be treated via method 900 include, but are not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like.

At 902, the method 900 can comprise disposing on a surface of an article the film-forming composition described herein. For example, the film-forming composition can comprise the star polymer 100 dispersed within a solvent. For instance, the star polymer 100 can comprise greater than or equal to 5 weight percent of the film-forming composition and less than or equal to 20 weight percent of the film-forming composition. Also, the star polymer 100 can comprise a core having a singlet oxygen generator (e.g., singlet oxygen generator core 104) and that can generate a singlet oxygen species upon irradiation with light. Further, the star polymer 100 can comprise a plurality of polycarbonate arms (e.g., arm 102) covalently bonded to the core (e.g., singlet oxygen generator core 104). Also, the plurality of polycarbonate arms (e.g., arm 102) can be degradable and comprise a cation (e.g., cationic functional group 204). Thus, the plurality of polycarbonate arms (e.g., arm 102) can have antimicrobial functionality.

The film-forming composition can be disposed on the surface via a variety of techniques including, but not limited to: dipping, spraying, spin coating, brushing, a combination thereof, and/or the like. In various embodiments, disposing the film-forming composition coats the surface of the article with an initial layer of star polymers 100 that are not crosslinked to other star polymers (e.g., other star polymers 100). At 904, the method 900 can comprise removing the solvent from the film-forming composition, and thereby, the surface of the coated article. The solvent can be removed via evaporation (e.g., by ambient conditions and/or a drying treatment, such as heated air). Upon removing the solvent, the star polymers 100 left residing on the surface of the article can begin to crosslink with each other, thereby forming a crosslinked film layer on the surface of the article.

At 906, the method 900 can optionally include a thermal and/or photochemical treatment of the surface to facilitate crosslinking between star polymers 100. The thickness of the crosslinked film layer of the star polymers 100 on the surface of the treated article can vary depending on the concentration of the film-forming composition and/or the dispersing technique. In one or more embodiments, the method 900 can form a crosslinked layer having a thickness substantially equivalent to one star polymer 100. In some embodiments, the method 900 can form a crosslinked layer having a thickness substantially equivalent to a plurality of star polymers 100. Additionally, the crosslinked film layer can exhibit an opacity greater than or equal to 0% and less than or equal to 100%, with any suitable light absorbing and/or light transmission properties. Further, the crosslinked film layer can be any hue, including, but not limited to, red, yellow, blue or combinations thereof.

In various embodiments, the crosslinked film formed by the method 900 can adhere to a variety of surface materials including, but not limited to: metal surfaces, glass surfaces, plastic surfaces, ceramic surfaces, wood surfaces, stone surfaces, textile surfaces, paper surfaces, cloth surfaces, concrete surfaces, synthetic fiber surfaces, organic fiber surfaces, a combination thereof, and/or the like. Furthermore, in one or more embodiments the crosslinked film layer can be treated with one or more chemical agents (e.g., alkylating agents) to increase the antimicrobial effect of the crosslinked film layer. In some embodiments, biocompatible forms of the star polymer 100 can be utilized with method 900 to form biocompatible crosslinked films that can surface treat insertable medical devices.

In one or more embodiments, the treated surface comprising the crosslinked film layer can be irradiated with light to facilitate on-demand enhanced antimicrobial functionality. For example, the singlet oxygen generator core 104 can generate one or more singlet oxygen species in response to the light. Subsequent to being irradiated with light, the crosslinked film layer can be recovered from the article's surface so as to recycle the star polymer 100.

Thus, in various embodiments a method 900 of forming a surface treated article can comprise disposing (e.g., at 902) on a surface of an article a film-forming composition. The film-forming composition can comprise a solvent (e.g., water and/or an organic solvent) and a star polymer (e.g., star polymer 100). The star polymer (e.g., star polymer 100) can comprise a singlet oxygen generator core 104 and a plurality of degradable polycarbonate arms 102. The singlet oxygen generator core 104 can be derived from a single oxygen generator molecule (e.g., a porphyrin, a phthalocyanine, a phenothiazine, a xanthene, and/or a quinone). Further, the singlet oxygen generator core 104 can comprise one or more linkage groups (e.g., second linkage group 302) to facilitate bonding of the degradable polycarbonate arms 102. The singlet oxygen generator core 104 can generate one or more singlet oxygen species in response to being irradiated with light (e.g., light having a wavelength greater than or equal to 10 nm and less than or equal to 750 nm). The plurality of degradable polycarbonate arms 102 (e.g., four polycarbonate arms 102) can be covalently bonded to the singlet oxygen generator core 104 (e.g., via the second linkage group 302). The plurality of polycarbonate arms 102 can comprise a cationic functional group 204 covalently bonded to a molecular backbone 202 (e.g., via the first linkage group 208). The cationic functional group 204 can comprise a nitrogen cation (e.g., a protonated primary amine cation, a protonated secondary amine cation, a protonated tertiary amine cation, a quaternary ammonium cation, and/or an imidazolium cation) and/or a phosphorus cation (e.g., a protonated primary phosphine cation, a protonated secondary phosphine cation, a protonated tertiary phosphine cation, a quaternary phosphonium cation). Further, the cationic functional group 204 can comprise a hydrophobic group (e.g., bonded to the cation). Additionally, the polycarbonate arms 102 can comprise a reactive end group 206 to facilitate a crosslinking between the star polymer (e.g., star polymer 100) and another star polymer (e.g., another star polymer 100). The film-forming composition can be toxic to a pathogen (e.g., a Gram-negative bacteria, a Gram-positive bacteria, fungi, and/or yeast). Also, the method 900 can comprise removing the solvent (e.g., at 904) from the surface of the article, and optionally applying a treatment (e.g., at 906) to the film-forming composition (e.g., a thermal treatment and/or a photochemical treatment).

FIG. 10 illustrates another flow diagram of an example, non-limiting method 1000 of killing a pathogen, preventing the growth of a pathogen, and/or preventing contamination by a pathogen. Repetitive description of like elements employed in other embodiments described herein is omitted for sake of brevity. Example pathogens include, but are not limited to: Gram-negative bacteria, Gram-positive bacteria, fungi, yeast, a combination thereof, and/or the like.

At 1002, the method 1000 can comprise contacting a pathogen with a polymer (e.g., one or more of the star polymers 100 and/or a crosslinked film formed on the surface of an article in accordance to method 900). For example, in accordance with various embodiments described herein, the polymer (e.g., a star polymer 100) can comprise a core having a singlet oxygen generator (e.g., singlet oxygen generator core 104) and that can generate a singlet oxygen species upon irradiation with light. Further, the polymer (e.g., star polymer 100) can comprise a plurality of polycarbonate arms (e.g., arm 102) covalently bonded to the core (e.g., singlet oxygen generator core 104). Also, the plurality of polycarbonate arms (e.g., arm 102) can be degradable and comprise a cation (e.g., cationic functional group 204). Thus, the plurality of polycarbonate arms (e.g., arm 102) can have antimicrobial functionality. In various embodiments, upon contact, the star polymer 100 can disrupt a membrane of the pathogen (e.g., via electrostatic disruption and/or hydrophobic integration). In one or more embodiments, the one or more star polymers 100 can be located on the surface of an article, whereupon the contacting can comprise a physical meeting of the article's treated surface with the pathogen. In some embodiments, the pathogen can be located on the surface of an article, whereupon the contacting can comprise a physical meeting of the one or more star polymers 100 with the pathogen. For example, the pathogen can be located on an article and the contacting at 1002 can comprise coating the contaminated article with the film-forming composition described herein. For instance, the pathogen can be located on a crop, wherein the contaminated crop can be sprayed with a film-forming composition comprising the star polymer 100.

At 1004, the method 1000 can further comprise irradiating one or more of the star polymers 100 in contact with the pathogen with light. For example, the light can have a wavelength greater than or equal to 10 nanometers and less than or equal to 750 nanometers. In various embodiments, the one or more star polymers 100 irradiated with light can respond by generating a singlet oxygen species (e.g., via the singlet oxygen generator core 104), wherein the singlet oxygen species can facilitate degradation of the pathogen. Thus, the antimicrobial effects of method 1000, and thereby the star polymer, can be increased on demand via controlled irradiation of the one or more star polymers with light.

Thus, in one or more embodiments a method 1000 of killing a pathogen can comprise contacting (e.g., at 1002) the pathogen with a polymer. The polymer (e.g., star polymer 100) can comprise a singlet oxygen generator core 104 and a plurality of degradable polycarbonate arms 102. The singlet oxygen generator core 104 can be derived from a single oxygen generator molecule (e.g., a porphyrin, a phthalocyanine, a phenothiazine, a xanthene, and/or a quinone). Further, the singlet oxygen generator core 104 can comprise one or more linkage groups (e.g., second linkage group 302) to facilitate bonding of the degradable polycarbonate arms 102. The singlet oxygen generator core 104 can generate one or more singlet oxygen species in response to being irradiated with light (e.g., light having a wavelength greater than or equal to 10 nm and less than or equal to 750 nm). The plurality of degradable polycarbonate arms 102 (e.g., four polycarbonate arms 102) can be covalently bonded to the singlet oxygen generator core 104 (e.g., via the second linkage group 302). The plurality of polycarbonate arms 102 can comprise a cationic functional group 204 covalently bonded to a molecular backbone 202 (e.g., via the first linkage group 208). The cationic functional group 204 can comprise a nitrogen cation (e.g., a protonated primary amine cation, a protonated secondary amine cation, a protonated tertiary amine cation, a quaternary ammonium cation, and/or an imidazolium cation) and/or a phosphorus cation (e.g., a protonated primary phosphine cation, a protonated secondary phosphine cation, a protonated tertiary phosphine cation, a quaternary phosphonium cation). Further, the cationic functional group 204 can comprise a hydrophobic group (e.g., bonded to the cation). Additionally, the polycarbonate arms 102 can comprise a reactive end group 206 to facilitate a crosslinkage between the star polymer (e.g., star polymer 100) and another star polymer (e.g., another star polymer 100). Upon contact with the pathogen, the polymer (e.g., star polymer 100) can disrupt a membrane of the pathogen (e.g., via electrostatic disruption and/or hydrophobic integration). The method 1000 can further comprise irradiating the polymer with the light (e.g., at 1004), thereby generating the singlet oxygen species via the singlet oxygen generator core 104 within the star polymer.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A polymer, comprising:
   a singlet oxygen generator core that generates a singlet oxygen species upon irradiation with light; and
   a plurality of polycarbonate arms covalently bonded to the singlet oxygen generator core, the plurality of polycarbonate arms being degradable and comprising a cation, wherein the plurality of polycarbonate arms have antimicrobial functionality.

2. The polymer of claim 1, wherein the singlet oxygen generator core is derived from a molecule selected from a group consisting of a porphyrin, a phthalocyanine, a phenothiazine, a xanthene and a quinone.

3. The polymer of claim 1, wherein the polymer comprises four polycarbonate arms.

4. The polymer of claim 1, wherein the cation is selected from a group consisting of a protonated primary amine cation, a protonated secondary amine cation, a protonated tertiary amine cation, a quaternary ammonium cation, an imidazolium cation, a protonated primary phosphine cation, a pronated secondary phosphine cation, a protonated tertiary phosphine cation and a quaternary phosphonium cation.

5. The polymer of claim 4, wherein the cation is the quaternary ammonium cation.

6. The polymer of claim 4, wherein the plurality of polycarbonate arms further comprise a hydrophobic group.

7. The polymer of claim 2, wherein the plurality of polycarbonate arms have a structure characterized by formula 1:

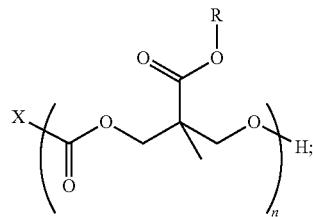

wherein X represents a connection to the singlet oxygen generator core; wherein R represents the cation selected from a first group consisting of a nitrogen cation and a phosphorus cation; wherein H is selected from a second group consisting of a hydrogen and a second functional group that facilitates crosslinkage of the polymer; and wherein n is an integer greater than or equal to 5 and less than or equal to 1000.

8. The polymer of claim 7, wherein the singlet oxygen generator core has a second structure characterized by formula 2:

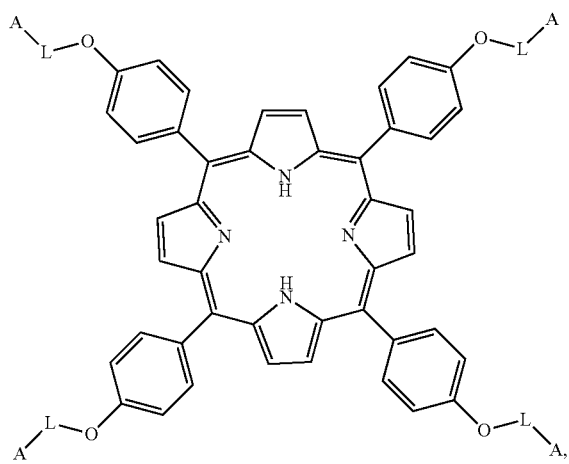

wherein L represents a linkage group comprising an ether group, and wherein A represents a polycarbonate arm from the plurality of polycarbonate arms.

9. The polymer of claim 1, wherein the polymer has a structure characterized by formula 1:

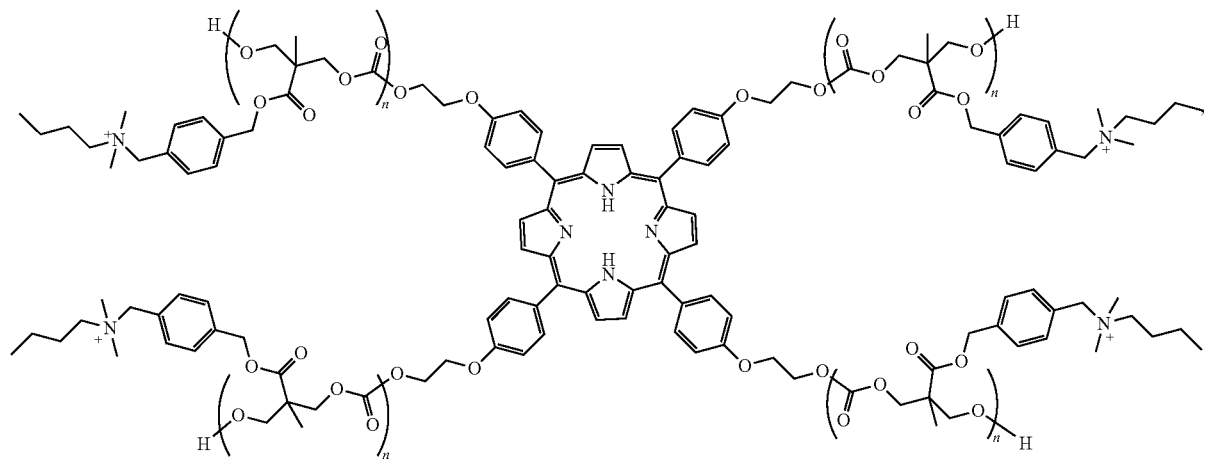

wherein n is an integer greater than or equal to 5 and less than or equal to 1000, and wherein H is selected from a group consisting of a hydrogen and a second functional group that facilitates crosslinkage of the polymer.

10. A method, comprising:
forming a plurality of degradable polycarbonate arms by polymerizing a plurality of carbonates with a singlet oxygen generator core, wherein the singlet oxygen generator core generates a singlet oxygen species in response to being irradiated with light; and
generating a cationic moiety by covalently bonding a functional group with a degradable polycarbonate arm from the plurality of degradable polycarbonate arms.

11. The method of claim 10, wherein the functional group can comprise a chemical structure selected from a group consisting of an amine, a phosphine and an imidazole.

12. The method of claim 11, wherein the generating comprises bonding the functional group to the degradable polycarbonate arm in a presence of an acetyl group.

13. The method of claim 12, wherein the degradable polycarbonate arm has a structure characterized by formula 1:

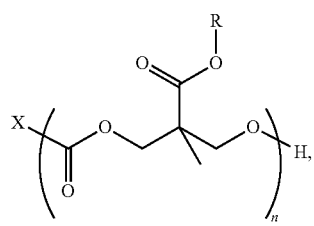

wherein X represents a connection to the singlet oxygen generator core, wherein R represents the cationic moiety, wherein n is an integer greater than or equal to 5 and less than or equal to 1000, and wherein H is selected from a second group consisting of a hydrogen and a third functional group that facilitates crosslinkage of the degradable polycarbonate arm.

14. The method of claim 13, further comprising preparing the singlet oxygen generator core by polymerizing a singlet oxygen generator molecule with a first functional group, wherein the singlet oxygen generator molecule is selected from a third group consisting of a porphyrin, a phthalocyanine, a phenothiazine, a xanthene and a quinone.

15. The method of claim 14, wherein the first functional group is an alcohol group and the prepared singlet oxygen generator core comprises a hydroxyl group.

16. A film-forming composition, comprising:
a solvent; and
a polymer comprising greater than or equal to 5 weight percent of the film-forming composition and less than or equal to 20 weight percent of the film-forming composition, the polymer dispersed in the solvent, and the polymer comprising:
a singlet oxygen generator core that generates a singlet oxygen species upon irradiation with light; and
a plurality of polycarbonate arms covalently bonded to the singlet oxygen generator core, the plurality of polycarbonate arms being degradable and comprising a cation, wherein the plurality of polycarbonate arms have antimicrobial functionality.

17. The film-forming composition of claim 16, wherein the film-forming composition is toxic to a pathogen selected from a group consisting of a Gram-negative bacteria, a Gram-positive bacteria, fungi and yeast.

18. The film-forming composition of claim 17, wherein the singlet oxygen generator core is derived from a molecule selected from a first group consisting of a porphyrin, a phthalocyanine, a phenothiazine, a xanthene and a quinone; and wherein the cation selected from a second group consisting of nitrogen cations and phosphorus cations.

19. A method of forming a surface treated article, comprising:
disposing (on a surface of an article a film-forming composition, the film-forming composition comprising:
a solvent; and
a polymer comprising greater than or equal to 5 weight percent of the film-forming composition and less than or equal to 20 weight percent of the film-forming composition, the polymer dispersed in the solvent, and the polymer comprising:
a singlet oxygen generator core that generates a singlet oxygen species upon irradiation with light; and
a plurality of polycarbonate arms covalently bonded to the singlet oxygen generator core, the plurality of polycarbonate arms being degradable and comprising a cation, wherein the plurality of polycarbonate arms have antimicrobial functionality; and
removing the solvent from the surface of the article.

20. The method of claim 19, wherein the film-forming composition is toxic to a pathogen selected from a group consisting of a Gram-negative bacteria, a Gram-positive bacteria, fungi and yeast.

21. The method of claim 20, wherein the singlet oxygen generator core is derived from a molecule selected from a first group consisting of a porphyrin, a phthalocyanine, a phenothiazine, a xanthene and a quinone; and wherein the cation selected from a second group consisting of a nitrogen cation and a phosphorus cation.

22. A method of killing a pathogen, comprising:
contacting the pathogen with a polymer, the polymer comprising:
a singlet oxygen generator core that generates a singlet oxygen species upon irradiation with light; and
a plurality of polycarbonate arms covalently bonded to the singlet oxygen generator core, the plurality of polycarbonate arms being degradable and comprising a cation, wherein the plurality of polycarbonate arms have antimicrobial functionality, and wherein the contacting of the pathogen with the polymer electrostatically disrupts a membrane of the pathogen.

23. The method of claim 22, further comprising:
irradiating the polymer with the light; and
generating the singlet oxygen species via the singlet oxygen generator core.

24. The method of claim 23, wherein the pathogen is selected from a group consisting of a Gram-negative bacteria, a Gram-positive bacteria, fungi and yeast.

25. The method of claim 24, wherein the singlet oxygen generator core is derived from a molecule selected from a first group consisting of a porphyrin, a phthalocyanine, a phenothiazine, a xanthene and a quinone; and wherein the cation selected from a second group consisting of a nitrogen cation and a phosphorus cation.

* * * * *